United States Patent [19]

Egorov et al.

[11] 4,186,590
[45] Feb. 5, 1980

[54] METHOD OF DETERMINING THE QUANTITATIVE CONTENT OF GASEOUS OR VAPOROUS IMPURITY IN A GAS MIXTURE AND A DEVICE FOR ACCOMPLISHING SAME

[76] Inventors: Alexandr F. Egorov, Shmidtovsky Proezd, 15, kv. 25; Vadim J. Ryzhnev, Ryazansky prospekt, 95, Korpus 4, kv. 20; Dmitry K. Simonovsky, ulitsa Vvedenskogo, 17, korpus 1, kv. 97; Valery A. Sokolov, ulitsa Malysheva, 4, kv. 30, all of Moscow, U.S.S.R.

[21] Appl. No.: 902,106

[22] Filed: May 2, 1978

[51] Int. Cl.$^2$ .............................................. G01N 7/00
[52] U.S. Cl. .................................................. 73/23
[58] Field of Search ............................. 73/23, 30, 32R

[56] References Cited
U.S. PATENT DOCUMENTS

| | | | |
|---|---|---|---|
| 3,592,042 | 7/1971 | Martinez | 73/23 |
| 3,783,676 | 1/1974 | Tanney | 73/32 R |
| 4,073,183 | 2/1978 | Byalko et al. | 73/23 |

FOREIGN PATENT DOCUMENTS 481814  10/1975  U.S.S.R. ...................................... 73/23

Primary Examiner—Stephen A. Kreitman
Attorney, Agent, or Firm—Fleit & Jacobson

[57] ABSTRACT

The method of the present invention provides for an acceleration of a gas mixture jet to supersonic velocity ensuring the emergence of a shock wave in the absence of impurity, the recording of the total head of said jet and determination of the impurity from a variation of the shock wave position and intensity.

The device for accomplishing said method comprises intercommunicated hollow bodies of a sensing element and of an ejector. Coaxially mounted in the walls of the sensing element body is a feed nozzle made in the form of a Laval nozzle and an inlet nozzle communicated with a vacuum meter. In the ejector walls there are coaxially arranged a mixing chamber communicated with a diffuser, and a working nozzle with a pressure regulator coupled thereto.

3 Claims, 1 Drawing Figure

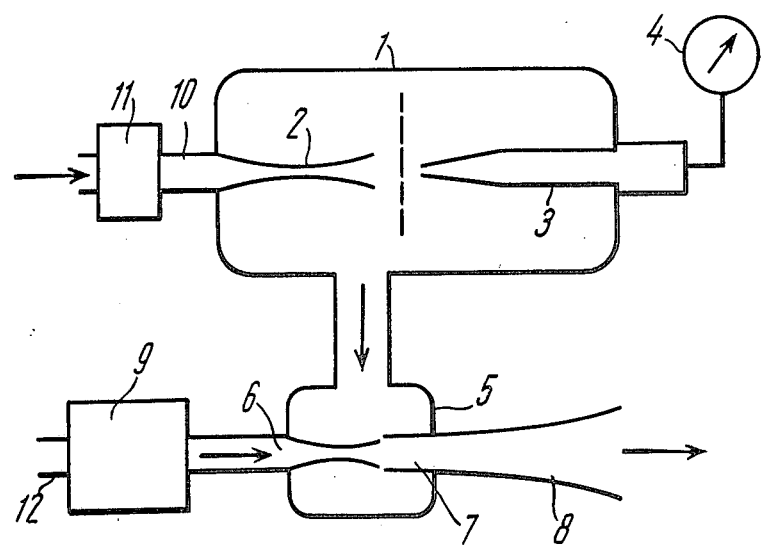

METHOD OF DETERMINING THE QUANTITATIVE CONTENT OF GASEOUS OR VAPOROUS IMPURITY IN A GAS MIXTURE AND A DEVICE FOR ACCOMPLISHING SAME

BACKGROUND OF THE INVENTION

The present invention relates to methods of determining the quantitative content of gaseous or vaporous impurity in a gas mixture and to devices for accomplishing said methods.

The present invention can be used most effectively for studying the composition and properties of substances in chemistry and petroleum chemistry as it provides fire and explosive safety and high corrosion resistance in aggressive mediums.

Known in the art are methods of determining the quantitative content of gaseous or vaporous impurity in a gas mixture, based on the agitation of a laminar jet upon the emergence of the impurity being determined. For example, in order to determine the quantitative content of impurity in a gas mixture, the latter is formed into a jet after which the total head of said jet is recorded.

However, said method is not sensitive enough to variations in the quantitative content of impurity in a gas mixture.

Known in the art are methods of determining the quantitative content of gaseous or vaporous impurity in a binary gas mixture, based on measuring the total head whose value depends on aerodynamic friction losses upon laminar flow of gas jet. Such a method is used for measurements when no high sensitivity is required, for example, in the synthesis of ammonia, at a hydrogen content in nitrogen of from 50 to 80 percent by volume. Some methods are based on variations in the jet head losses upon transition from laminar to turbulent flow. Such methods are utilized in instruments designed to meet higher sensitivity requirements, for example, in indicators of the presence of oil vapors in the air in a concentration of from 0.3 to 0.5 percent by volume.

U.S.S.R. Inventor's Certificate No. 332,453 discloses a pneumatic indicator comprising: channels for the delivery of a gas being analyzed and reference gas; a sensing element comprising a feed capillary and an inlet tube, both arranged coaxially in a common housing, the inner space of the housing being coupled with a suction device; a comparison element, one of whose inputs is coupled with the sensing element output; an oscillator; a "throttle-receptacle" link; a power amplifier and an output channel. Said indicator differs from other prior art in that it comprises switches at the sensing element input and at the comparison element output, the two inputs of the first one of said switches being connected with the channels for the delivery of the gas being analyzed and of reference gas, respectively, while the first output of the second switch is connected via power amplifier to the indicator output channel and the second output is connected via "throttle-receptacle" link to the comparison element input, the receptacle in said latter link containing a dividing diaphragm whose control space is coupled with the oscillator output connected, in turn, to the control inputs of both switches.

Said pneumatic indicator comprises, as seen from the aforecited claim, a large number of elements, which tends to complicate the instrument and affect its reliability. Such devices are noted for their complicated circuits designed primarily to maintain the working parameters of the sensing elements upon variation of ambient temperature or of feed air pressure.

U.S.S.R. Inventor's Certificate No. 395,723 discloses a pneumatic gas analyzer-and-indicator comprising a fluid-jet sensing element whose input is coulped via first switch with channels for gas being analyzed and for reference gas, an ejector whose input is coupled to the sensing element chamber, a comparison element whose one input is connected to the sensing element output, and a timing pulse generator connected with two switches. Said prior art device is distinguished in that it is provided with a damping link and a throttle divider whose input is coupled with the ejector input while the output is connected with the second input of the comparison element whose output is connected via second switch to an output channel of the device and, via damping link, to the ejector control channel.

Said pneumatic gas analyzer-and-indicator is structurally simpler than that disclosed in U.S.S.R. Inventor's Certificate No. 332,453, however, its sensitivity to impurities being analyzed is much lower.

Most of the prior art instruments are characterized by complicated circuitry involving a large number of diaphragm elements which affect considerably the reliability of the instrument operation and complicate their manufacture and repair.

An intensive development of chemical industry places stricter requirements upon the sensitivity of methods and means of measuring impurities in gas mixtures.

For example, the presence of moisture in processes involving chlorine-containing materials results in premature corrosion of the equipment, decomposition of catalysts and deterioration of the quality of produce.

Neither prior art methods based on the laminar flow of a gas mixture jet, nor those based on the transition from laminar to turbulent flow, can meet modern technological requirements.

Similar difficulties are encountered when using prior art instruments for accomplishing the afore-listed methods.

The absence of structurally simple and reliable devices for realization above-mentioned methods makes it rather difficult to determine impurities in gas mixtures.

SUMMARY OF THE INVENTION

The main object of the present invention is to provide a method of determining the quantitative content of gaseous or vaporous impurity in a gas mixture and a device for accomplishing said method, which would ensure an increased sensitivity to variations in the quantitative content of the impurity in the gas mixture while the device would be simpler structurally and more reliable in operation than the prior art devices.

Said and other objects can be attained in a method of determining the quantitative content of gaseous or vaporous impurity in a gas mixture, involving the formation of a gas mixture jet with subsequent recording of the total head of said jet, wherein, according to the invention, the gas mixture jet is accelerated to supersonic velocity ensuring the emergence of a shock wave in the absence of impurity, the desired impurity value being found from a variation of the shock wave intensity.

The gas mixture jet is accelerated to supersonic velocity by means of a Laval nozzle employed in the device for accomplishing the method of the invention. It is known from gas dynamics that a shock wave located in the flow-through portion of the nozzle may lose stability and move along the nozzle axis depending on the pressure behind the nozzle. It is the utilization of this phenomenon that forms the basis of the method of the present invention providing for the emergence of a shock wave in the absence of impurity and providing quite a simple way of finding the desired impurity value from a variation of the shock wave intensity, and its position along the axis of the nozzle.

In this case, gas flow conditions are set up in the Laval nozzle which provide for a shock wave state close to the loss of stability.

Upon occurrence of the impurity being analyzed (gas, water vapors, alcohol vapors, etc), the shock wave loses stability and moves with the flow towards the outlet end face (flow area) of the Laval nozzle. On getting into the opening of the Laval nozzle, where the end face of an inlet tube may be located, the shock wave acts to sharply increase the static pressure whose value depends upon the shock wave intensity in this area, which is taken up by the inlet tube as an output signal of the device.

The value of static pressure after the shock wave (a parameter affecting the magnitude of the signal) depends upon the shock wave intensity affected by the undisturbed flow velocity which, in turn, depends primarily upon the concentration of components being analyzed.

The herein disclosed method can be accomplished in a device according to the invention, comprising a hollow body of a sensing element in whose opposite walls there are coaxially mounted a feed nozzle made in the form of a Laval nozzle and an inlet nozzle communicated with a vacuum meter, the space of the sensing element body being communicated with the space of an ejector body in whose opposite walls there are coaxially arranged a mixing chamber communicated with a diffuser and a working nozzle with a pressure regulator coupled thereto.

The provision of the feed nozzle made in the form of a Laval nozzle helps accelerate a gas mixture jet to supersonic velocity.

In addition, the inlet nozzle serves an obstacle to the supersonic flow of gas mixture and is conducive to the emergence of a shock wave. The presence of the pressure regulator connected to the ejector working nozzle helps attain a shock wave state in the Laval nozzle close to the loss of stability.

Upon occurrence of impurity in the gas mixture, the shock wave loses stability and moves towards the inlet tube (towards the outlet end face of the Laval nozzle). At the same time, the shock wave intensity varies (i.e., the value of static pressure after the shock wave).

Upon the approach of shock wave to the end face of the inlet tube, the shock wave position is stabilized while the increase of static pressure caused by the shock wave in the aforementioned portion of the Laval nozzle serves an output signal indicative of the presence of gaseous or vaporous impurity.

The instrument of the present invention is insensitive to ambient temperature variations within 10° to 35° C.

This is due to the fact that the shock wave shift under the effect of temperature is negligible and the shock wave fails to reach the end face of the inlet tube, and no pressure variations occur in the tube as a result.

The present invention will be better understood upon considering the following description of an exemplary embodiment thereof, relating to the method and device of the invention, with due references to the accompanying drawing which shows diagrammatically the device of the invention for determining the quantitative content of gaseous or vaporous impurity in a gas mixture.

The method of the invention of determining the quantitative content of gaseous or vaporous impurity in a gas mixture provides for the formation of a gas mixture jet with subsequent recording of the total head of said jet accelerated to supersonic velocity. Under conditions of such velocity and in the absence of impurity, in the gas mixture jet there emerges a shock wave from the variation of whose position and intensity the desired impurity value is found.

In case a gaseous or vaporous impurity is detected in the gas mixture being analyzed, the degree of vacuum in the inlet nozzle of the device is reduced (described below in more detail), which is measured by a vacuum meter from whose readings the impurity value is found.

BRIEF DESCRIPTION OF THE DRAWING

The only FIGURE in the drawing shows the apparatus for determining the quantitative content of gaseous or vaporous impurity in a gas mixture.

DETAILED DESCRIPTION OF THE INVENTION

The device for accomplishing the method of the invention comprises a hollow body 1 of a sensing element, in whose opposite walls there are mounted a feed nozzle 2 made in the form of a Laval nozzle and an inlet nozzle 3, said nozzles arranged coaxially with each other.

The inlet nozzle 3 is communicated with a vacuum measuring instrument 4. The sensing element body 1 is communicated with a hollow body 5 of an ejector, in whose opposite walls there are coaxially arranged a working nozzle 6 and a mixing chamber 7 with a diffuser 8, a pressure regulator 9 being connected to the working nozzle 6 of the ejector. Provided at the inlet of the feed nozzle 2 is a pipe 10 for stabilizing the flow velocity distribution with a filter 11 at the inlet to said pipe.

A feed pipe 12 is provided for the delivery of compressed air to the pressure regulator 9.

The device for accomplishing the method of the invention operates in the following manner.

Compressed air is delivered via the feed pipe 12 and through the pressure regulator 9 to the working nozzle 6 of the ejector. With the aid of the latter, the gas mixture being analyzed is conveyed via the filter 11 and stabilizing pipe 10 to the inlet of the supersonic feed nozzle 2 in which the gas mixture flow is accelerated to supersonic velocity and a shock wave is generated by hitting the flow against the end face of the inlet nozzle 3, while monitoring the total head by the vacuum measuring instrument 4 such as vacuum meter.

Upon penetration of an impurity (gas or vapor) in the gas mixture being analyzed, the position and intensity of the shock wave vary, which results in a variation of the total head taken up by the inlet nozzle 3.

It is known from aerodynamics that the shock wave position in a supersonic flow, for example, relative to the Laval nozzle throat section, may vary with the pressure after the nozzle. For example, an increase of the pressure after the nozzle causes the shock wave to shift towards the throat section of the Laval nozzle, while a pressure decrease causes it to shift towards the outlet (in the direction of flow). There exists a critical state of the flow (and a corresponding degree of decompression after the nozzle) at which a slight variation of pressure in the sensing element body 1 (presence of impurities) causes a sharp variation of the shock wave position and intensity (the shock wave moves in the direction of the inlet nozzle 3) which is indicated by a sharp variation of total pressure at the end face of the inlet nozzle 3. This latter pressure variation serves an output signal of the device.

Tests have shown the device sensitivity to water and alcohol vapors to be in the range of from 0.04 to 0.05 percent by volume.

What is claimed is:

1. A device for determining the quantitative content of gaseous or vaporous impurity in a gas mixture, comprising: a hollow body of a sensing element; a feed nozzle made in the form of a Laval nozzle and mounted in a wall of said sensing element body; an inlet nozzle arranged coaxially with said feed nozzle and mounted in the opposite wall of said hollow body of a sensing element; a hollow body of an ejector, communicated with the space of said sensing element body; a working nozzle fixed in a wall of said hollow ejector body; a pressure regulator connected to said working nozzle; a body of a mixing chamber, arranged coaxially with said working nozzle and fixed in the opposite wall of said hollow ejector body; a diffuser located on the outside of said hollow ejector body and communicated with said mixing chamber; and a vacuum measuring instrument communicated with said inlet nozzle.

2. A method of determining the quantitative content of gaseous or vaporous impurity in a gas mixture, comprising the steps of forming a gas mixture jet, accelerating said jet to a supersonic velocity value to form a shock wave in the absence of impurities that is stabilized with respect to position and intensity, but close to the point at which the shock wave loses stability when impurities are present in the gas mixture, recording the total head after the shock wave downstream, and determining the impurity content according to the change in shock wave position and intensity caused by the presence of impurities in the gas mixture by recording the total head in the presence of impurities, wherein the variation in the total head before and after the appearance of impurities is proportional to the amount of impurities present in the gas mixture.

3. A method of determining the quantitative content of gaseous or vaporous impurity in a gas mixture, comprising the steps of positioning a feed nozzle in a hollow body wall, positioning an inlet nozzle in the opposite wall of the hollow body and coaxial with the feed nozzle, accelerating a gas mixture free of impurity at a supersonic velocity through the feed nozzle to create a shock wave in the hollow body that is stabilized in its position and intensity, but close to the point at which it loses stability when impurities are present in the gas mixture, measuring the pressure within the hollow body at the inlet nozzle, and measuring variations of said pressure within the hollow body at the inlet nozzle, wherein said pressure variations are proportional to the variations of the shock wave position and intensity and thus proportional to the presence of impurities in the accelerated gas mixture.

* * * * *